United States Patent [19]
Bank et al.

[11] Patent Number: 5,278,056
[45] Date of Patent: Jan. 11, 1994

[54] RETROVIRAL PACKAGING CELL LINES AND PROCESS OF USING SAME

[75] Inventors: Arthur Bank, Riverdale; Dina G. Markowitz, New York, both of N.Y.; Stephen P. Goff, Tenafly, N.J.

[73] Assignee: The Trustees of Columbia University in the City of New York, New York, N.Y.

[21] Appl. No.: 877,269

[22] Filed: Apr. 29, 1992

Related U.S. Application Data

[63] Continuation of Ser. No. 749,636, Aug. 19, 1991, abandoned, which is a continuation of Ser. No. 609,003, Oct. 29, 1990, abandoned, which is a continuation of Ser. No. 152,830, Feb. 5, 1988, abandoned.

[51] Int. Cl.$^5$ ........................ C12N 5/06; C12N 15/86
[52] U.S. Cl. ................... 435/172.3; 435/240.1; 435/240.2; 935/57; 935/70; 935/71
[58] Field of Search ............... 435/240.2, 172.3, 240.1

[56] References Cited

U.S. PATENT DOCUMENTS

| | | | |
|---|---|---|---|
| 4,650,764 | 3/1987 | Tomin et al. | 435/240 |
| 4,861,719 | 8/1989 | Miller | 435/236 |

OTHER PUBLICATIONS

Watanabe et al (1983) *Mol Cell Biol* 3:2241–2249.
Miller et al (1986) *Som Cell Mol Genet* 12:175–183.
Mann et al (1983) *Cell* 33:153–159.
Efstratiatis et al (1977) *Cell* 10:571–586 CAS Abstract included (CA 87(3):17475c.
Pouwels et al eds (1985) in *Cloning Vectors* (8 pages).
R. Dornburg et al (1988) *Mol. Cell. Biol* 8(6):2328–2334.
D. D. Muenchau et al (1990) *Virology* 176:262–265.
R. A. Hock et al. (1986) *Nature*, 320:275.
R. C. Mulligan and P. Berg, (1980) *Science*, 209:1422.
G. Keller et al., (1985) *Nature*, 318:145.
H. E. Gruber et al., (1985) *Science*, 230:237.
D. A. Williams et al. (1984) *Nature*, 310:476.
D. A. Williams et al. (1986) *Science*, 83:2566.
M. A. Eglitis et al. (1985) *Science*, 230:1395.

*Primary Examiner*—Elizabeth C. Weimar
*Assistant Examiner*—Johnny F. Railey, II
*Attorney, Agent, or Firm*—John P. White

[57] ABSTRACT

The invention relates to a mammalian cell line useful for retroviral packaging comprising two plasmids, the first such plasmid comprising in 5' to 3' order: a DNA sequence comprising a 5' long terminal repeat (LTR); a mutated ψ packaging sequence; a DNA sequence comprising the encoding portion of the Moloney murine leukemia virus (MULV) env gene; and the second such plasmid comprising in 5' to 3' order: a DNA sequence comprising a 5' long terminal repeat (LTR); a mutated ψ packaging sequence; a DNA sequence comprising the encoding portion of the Moloney murine leukemia virus (MULV) gag and pol genes; a selectable marker; and an origin of replication.

The invention also relates to processes for preparing a producer cell line useful for transferring a gene of interest into recipient mammalian cells in vitro.

9 Claims, 5 Drawing Sheets

☐ = SOLID REGIONS

= SOLID REGIONS

RETROVIRAL PACKAGING CELL LINES AND PROCESS OF USING SAME

The invention described herein was made in the course of work under Public Health Services grants DK-25274, HL-37069, and HL-07230 from the National Institutes of Health, U.S. Department of Health and Human Services. The U.S. Government has certain rights in this invention.

This application is a continuation of U.S. Ser. No. 749,636, filed Aug. 19, 1991, now abandoned, which is a continuation application of U.S. Ser. No. 609,003, filed Oct. 29, 1990, now abandoned, which is a continuation application of U.S. Ser. No. 152,830, filed Feb. 5, 1988, now abandoned.

BACKGROUND OF THE INVENTION

Throughout this application, various publications are referenced in parentheses and citations provided for them. The disclosure of these publications in their entireties are hereby incorporated by reference into this application to more fully describe the state of the art to which this invention pertains.

Retroviruses appear to be the method of choice as vectors for the transfer of exogenous genes into humans. In particular, the cloning, transfer, and expression of human globin genes into erythroid cells in culture has raised the possibility of autotransplantation of bone marrow cells with normal $\beta$-globin genes as an approach to the therapy of $\beta$-thalassemia and sickle cell anemia in humans (1). Retroviral vectors are the most efficient means of transferring genes into cells. This high efficiency is a requirement for experiments whose goal is human globin gene therapy because only a limited number of bone marrow stem cells can be obtained, and as many as possible must acquire and express the transferred genes to ensure repopulation of sufficient marrow elements to produce normal amounts of hemaglobin.

A major prerequisite for the use of retroviruses is to insure the safety of their use (2). The major danger of the use of retroviruses for gene therapy is the possibility of the spread of wild-type retrovirus in the cell population. The proliferation of wild-type virus can lead to multiple integrations of the retrovirus into the genome which may result in the activation of potentially harmful genes such as oncogenes (3, 4). The development of packaging cell lines that produce only replication-defective retroviruse:; has increased the utility of retroviruses for gene therapy (5–9). In these cell lines, the sequence required for packaging of the viral RNA ($\psi$ sequence) bias been deleted, therefore the packaging cell produces viral proteins but is unable to package the viral RNA genome into infectious virions. When these packaging lines are transfected with a replication-defective retroviral vector containing an intact $\psi$ sequence required for its own packaging, wild-type retrovirus has been shown to arise (6, 10, 11) presumably due to recombination events between the helper virus genome and the vector virus. For example, high titer amphotropic retroviral stocks generated by transfer of a defective neomycin-containing retrovirus into the amphotropic packaging cell line PA12 (containing the $\psi$ deletion) have been shown to produce infectious amphotropic helper virus (10, 11). To circumvent this problem, additional mutations have been made in the defective virus of newer helper cell lines (11). These have included deletions in the 3' LTR of the helper virus component, and additional deletions of portions of the 5' LTR as well. One of these defective amphotropic constructs has been used to produce a retroviral packaging line, PA317, that has recently been reported to eliminate wild type retrovirus production after retroviral transfection. However, using this packaging line, two recombinational events could still produce intact retrovirus. Cell lines containing both 3' and 5' LTR deletions as well as the packaging mutation were also constructed but were not useful because of the relatively low titers obtained with these constructs.

We have created novel ecotropic and amphotropic retrovirus packaging cell lines which should virtually eliminate the possibility of recombination between the helper virus and the vector virus leading to wild-type retrovirus. In our cell lines, the helper virus DNA has been separated onto two plasmids; the gag and the pol genes are on one plasmid and the env gene is on another plasmid. In addition, the packaging sequence and the 3' LTR have been deleted in both plasmids. With this type of strategy at least three recombination events between the two helper plasmids and the vector virus are necessary to generate a wild-type virus. We will describe the development of both a stable ecotropic and a stable amphotropic packaging line that are both efficient and safe for use in gene transfer experiments. An ecotropic packaging line concerns a virus which can only infect or transfect cells of the same species. In an amphotropic packaging line, the virus can infect or transfect a wide range of host cell species.

SUMMARY OF THE INVENTION

The present invention concerns a mammalian cell line useful for retroviral packaging comprising two plasmids, the first such plasmid comprising in 5' to 3' order; a DNA sequence comprising a 5' long terminal repeat (LTR); a mutated $\psi$ packaging sequence; a DNA sequence comprising the encoding portion of the Moloney murine leukemia virus (MULV) env gene; and the second such plasmid comprising in 5' to 3' order: a DNA sequence comprising a 5' long terminal repeat (LTR); a mutated $\psi$ packaging sequence; a DNA sequence comprising the encoding portion of the Moloney murine leukemia virus (MULV) gag and pol genes; a selectable marker; and an origin of replication.

This invention also provides a process for preparing a producer cell line useful for transferring a gene of interest into recipient mammalian cells comprising: treating mammalian cells belonging to the cell line, above-described, with a vector plasmid which comprises: a DNA sequence which includes a $\psi$ packaging sequence and 5' and 3' long terminal repeats (LTRs), a DNA sequence which contains a gene associated with a selectable or identifiable phenotypic trait which is manifested when the plasmid is present in a transfected cell, and a DNA sequence which contains a gene of interest to prepare producer cells; and recovering the producer cells.

This invention also provides process for transferring a gene of interest into recipient mammalian cells comprising: treating mammalian cells belonging to the cell line the previously described mammalian cell line useful for retroviral packaging with a vector plasmid which comprises a DNA sequence which includes a $\psi$ packaging sequence; and 5' and 3' long terminal repeats (LTRS) a DNA sequence which contains a gene associated with a selectable or identifiable phenotypic trait which is manifested when the plasmid is present in a transfected cell; and a DNA sequence which contains a gene of interest to prepare producer cells; and recovering the producer cells treating the recipient mammalian cells with the recovered producer cells thereby transferring a gene of interest.

BRIEF DESCRIPTION OF THE FIGURES

Mo-MULV LTRs and ψ deletion are indicated. Solid regions represent gag sequences; open regions represent pol sequences; hatched regions represent env or envAm sequences; wavy lines represent pBR322 sequences.

Wavy lines, pBR322 seqences; thin lines, plasmid sequences; small solid box, SV40 poly A sequences; SV, SV40 origin of replication; ψ—, deletion of ψ packaging sequences; Ba, Bam HI; Bg, Bgl II; E, Eco RI: Na, Nae I; Nh, Nhe I; S, Sca I.

ψ, packaging sequence; wavy line, pBR322 seqences; solid box, SV40 promoter and origin of replication.

Individual clones resistant to MA were isolated, and the supernatant fluids were assayed for reverse transcriptase on an exogenous template (14). Results are shown from two different experiments (top and bottom lines). Included in each experiment are positive ($\psi^2$ supernatant) and negative (3T3 supernatant) controls.

Plasmids pgag-polgpt and penv were cotransfected into 3T3 cells. Individual clones resistant to MA and which express high levels of RT were labelled with [$^{35}$S] methionine. The labelled proteins were analyzed by immunoprecipitation, sodium dodecyl sulfate gel electrophoresis, and fluorography as described in Methods. Lane 1: Proteins from 3PO-18 cells. Lanes 2-16: Proteins from GP+E clones 5, 21, 30, 37, 38, 41, 42, 43, 46, 56, 58, 66, 69, 75 and 86, respectively. The position of protein gPr80$^{env}$ is indicated by the arrow.

DETAILED DESCRIPTION OF THE INVENTION

A mammalian cell line useful for retroviral packaging comprising two plasmids, the first such plasmid comprising in 5' to 3' order: a DNA sequence comprising a 5' long terminal repeat (LTR); a mutated ψ packaging sequence; a DNA sequence comprising the encoding portion of the Moloney murine leukemia virus (MULV) env gene; and the second such plasmid comprising in 5' to 3' order: a DNA sequence comprising a 5' long terminal repeat (LTR); a mutated ψ packaging sequence; a DNA sequence comprising the encoding portion of the Moloney murine leukemia virus (MULV) gag and pol genes; a selectable marker such as drug resistance and an origin of replication, e.g. SV40.

The mammalian cell line which is produced by this invention may be ecotropic or amphotropic depending upon the plasmids which are employed. In one embodiment an ecotropic cell line is produced wherein the first plasmid is designated penv and has the restriction map shown in FIG. 2 and wherein the second plasmid is designated pgag-polgpt and has the restriction map shown in FIG. 2. Such ecotropic cell line is designated as GP+E-86 which has been deposited pursuant to the Budapest Treaty with the American Type Culture Collection (ATCC), Rockville, Md. under ATCC Accession No. CRL9642.

Figure 2:
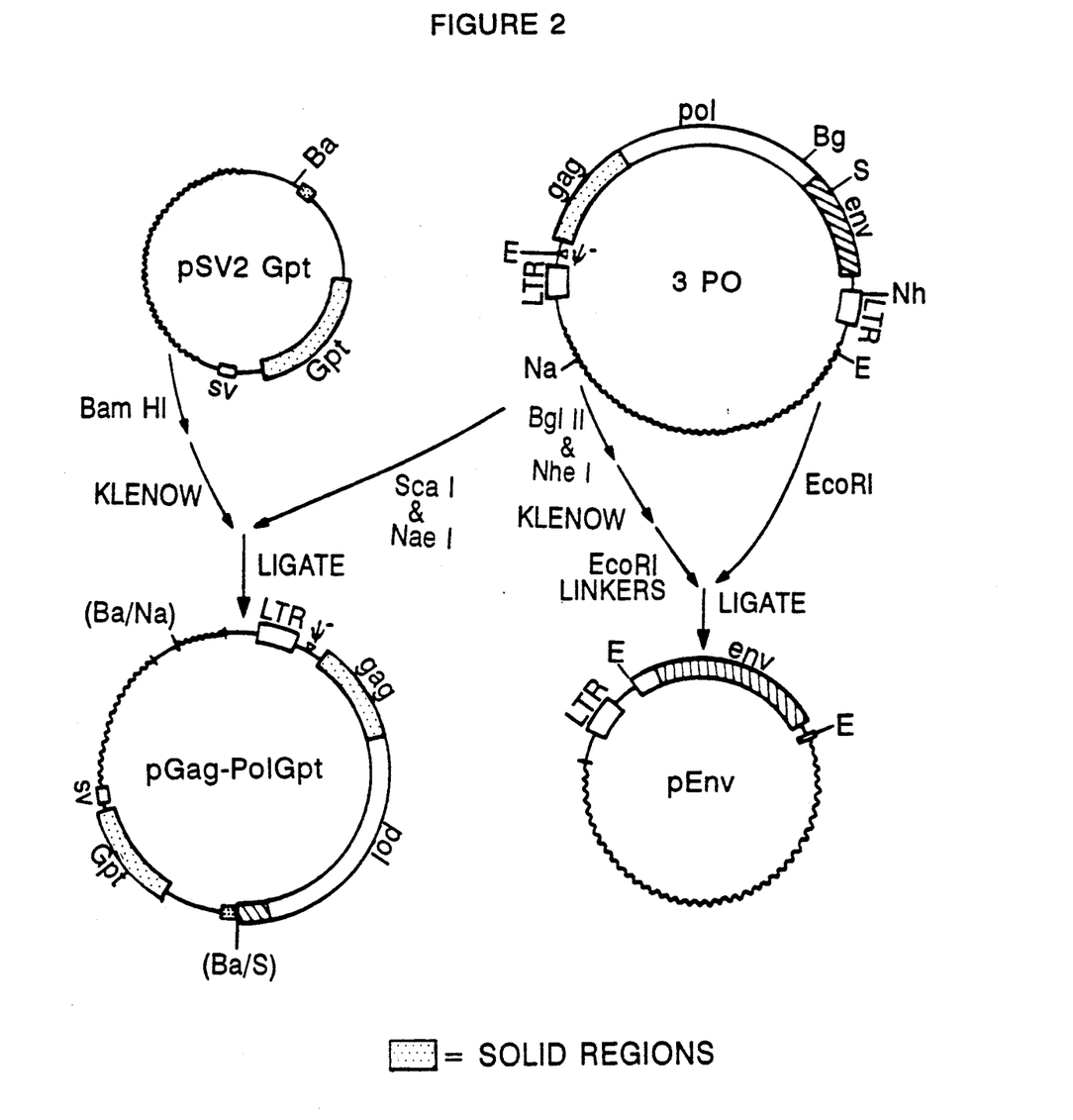
FIG. 2. Schematic diagram showing construction of plasmids pgag-polgpt and penv.

In another embodiment an amphotropic cell line is produced wherein the first plasmid is designated penvAm and has the restriction map shown in FIG. 2 and the second plasmid is designated pgag-polgpt and has the restriction map shown in FIG. 2. Such an amphotropic cell line is designated GP+envAm-12 and which has been deposited pursuant to the Budapest Treaty with the American Type Culture Collection (ATCC) under ATCC Accession No. CRL9641.

A mammalian cell useful in the practice of this invention is a mouse fibroblast in one embodiment the mouse fibroblast is a NIH 3T3 cell.

This invention also provides a process for preparing a producer cell line useful for transferring a gene of interest into recipient mammalian cells comprising: a treating mammalian cells belonging to the cell line of claim 1 with a vector plasmid which comprises: a DNA sequence which includes a ψ packaging sequence and 5' and 3' long terminal repeats (LTRs), a DNA sequence which contains a gene associated with a selectable or identifiable phenotypic trait which is manifested when the plasmid is present in a transfected cell, and a DNA sequence which contains a gene of interest to prepare producer cells; and recovering the producer cells. Treating may be effected by transfection.

Two mammalian cells useful in the above-described process belong to the cell lines designated GP+envAm-12 and GP+E-86 which have been deposited pursuant to the Budapest Treaty with the American Type Culture Collection (ATCC), Rockville, Md. under ATCC Accession Numbers CRL9641 and ATCC NO CRL 9642.

Two vector plasmids useful in the above-described process are Δneo and N2.

A useful phenotypic trait employed in the above-described process is drug resistance. An example of a gene of interest is the normal β globin gene.

The present invention also provides a process for transferring a gene of interest into recipient mammalian cells comprising: treating mammalian cells belonging to the cell line, above-described with a vector plasmid which comprises a DNA sequence which includes a ψ packaging sequence, and 5' and 3' long terminal repeats (LTRS) a DNA sequence which-contains a gene associated with a selectable or identifiable phenotypic trait which is manifested when the plasmid is present in a treated cell, and a DNA sequence which contains a gene of interest, e.g., normal β globin gene; to prepare producer cells; recovering the producer cells; and treating the recipient mammalian cells with the recovered producer cells thereby transferring a gene of interest.

The invention is illustrated in the Experimental Detail and Experimental Discussion sections which follow. These sections are set forth to aid in an understanding of the invention but are not intended to, and shall not be construed to, limit in any way the invention as set forth in the claims which follow thereafter.

EXPERIMENTAL DETAILS

Materials and Methods

Generation of Ecotropic Packaging Line

Figure 1:
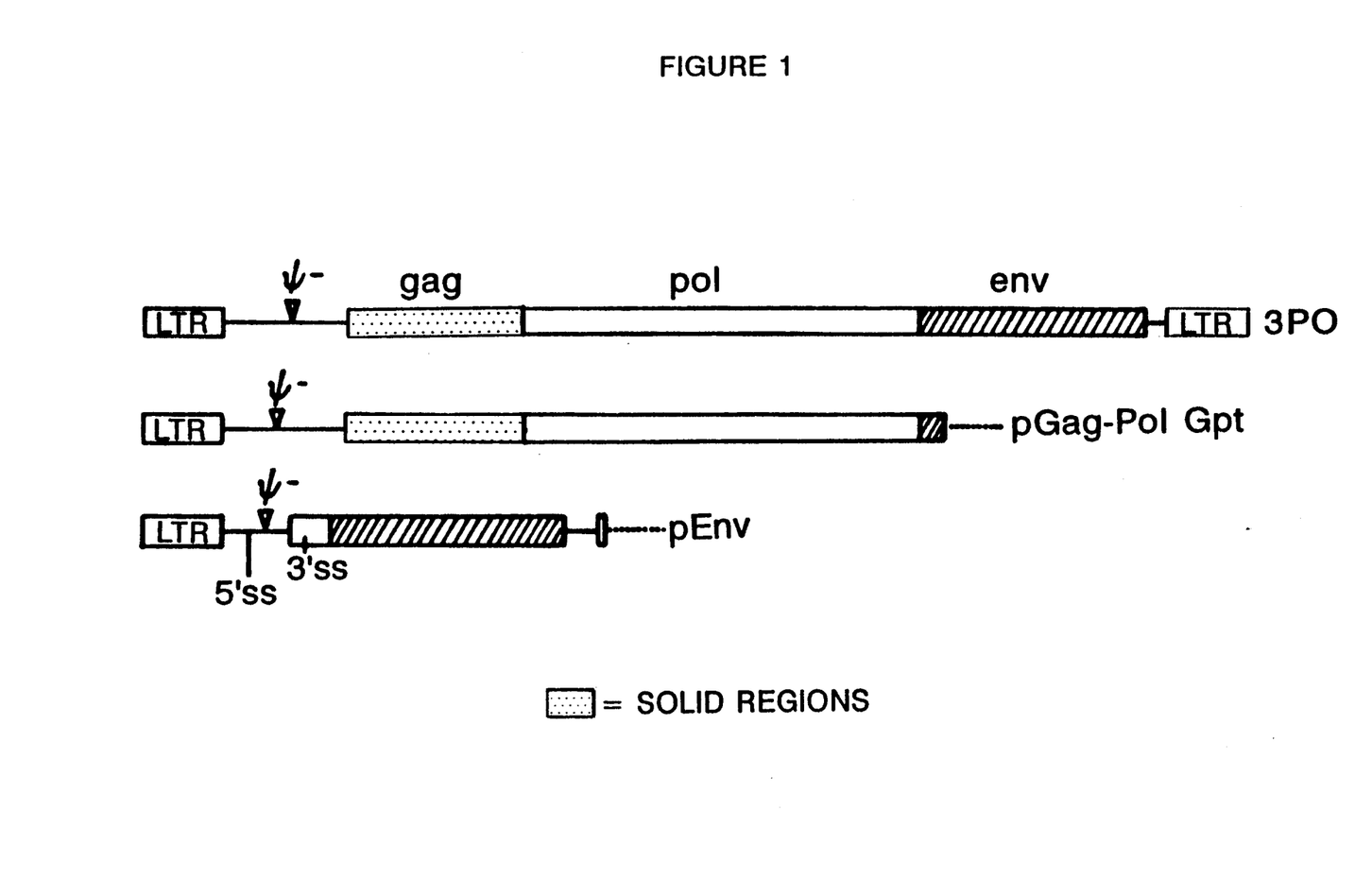
FIG. 1. Comparison of viral sequences contained in parent plasmid 3PO and constructs pgag-polgpt, penv and penvAm.

To generate an ecotropic packaging cell line two helper virus plasmids, pgag-polgpt and penv, were constructed using Mo-MULV proviral DNA from the plasmid 3PO as starting material (FIG. 1).

pgag-polgpt pgag-polgpt (FIG. 1) was constructed by isolating a fragment containing the 5' LTR and the gag and pol DNA and inserting this fragment into the plasmid pSV2gpt (12) which was used as the source of SV40 sequences and the gpt gene as a selectable marker.

The plasmid 3PO contains Mo-MULV proviral DNA with a 134 base pair deletion of the $\psi$ packaging signal, from Bal I 660 to Xma III 792 (L. Lobel and S. Goff, personal communication). 3PO DNA was digested with Sca I and Nae I, both leaving blunt ends, and a 7.9 kilobase (kb) fragment containing the 5' LTR and the gag and pol genes were isolated from a 1.7% agarose gel by electroelution. Plasmid pSV2gpt was digested at its unique Bam HI site, and its protruding 5' ends filled by using the Klenow fragment of DNA polymerase and all four dNTPs. The 7.9 kb gag-pol fragment was then ligated to the blunt-ended 5.1 kb pSV2gpt vector, and positive colonies were isolated using colony filter hybridization (18), probing with a nick-translated 2.54 kb Bgl II fragment for 3PO (gag-pol probe). DNAs from individual colonies were then tested for the correct orientation of the gag-pol insert by digesting with Eco RI. The resulting 13.4 kb plasmid was named pgag-polgpt (FIG. 2).

penv:

penv (FIG. 1) was constructed by isolating a fragment from 3PO that contains the 3' acceptor splice site and the env gene and the ligating it to another fragment from 3PO containing the 5' LTR and 5' donor splice site.

First, the plasmid 3PO was digested with Bgl II and Nhe I (FIG. 2). The 2.4 kb env fragment 5858 to 8297 containing the 3' acceptor splice site was isolated by electroelution from a 1.2% agarose gel. The ends were filled with the Klenow fragment of DNA polymerase and all four dNTPs, and Eco RI linkers were ligated to both ends. The 5' LTR and 5' donor splice site were prepared by digesting 3PO DNA with Eco RI, and isolating the 6.2 kb fragment by electroelution from a 1% agarose gel. The 6.2 kb fragment was phosphatased, and then ligated to the 2.4 kb env fragment. Positive transformants were isolated using the colony filter hybridization technique probed with a labelled 1.2 kb Hpa I fragment from 3PO (env probe). DNAs from positive colonies were then tested for the correct orientation of the env insert by digesting with either Xba I or Sca I. The resulting 8.6 kb plasmid was named penv (FIG. 2).

Electroporation and Cell Analysis

NIH 3T3 Cells were transfected with pgag-polgpt or the penv plasmid by electroporation (13). For each experiment, $10^7$ cells were collected by centrifugation, and resuspended in 0.5 ml sterile 1×PBS. The cells were then mixed with $10^7$ $\mu$g nonselectable plasmid DNA and/or 5 $\mu$g selectable plasmid DNA. The cell/DNA suspension was loaded into a 0.5 ml electroporation chamber (PDS model ZA1000, Madison, Wis.) and a bank of capaciters (effective capacity 14UF), charged to 500–1,000 volts, and discharged via an electronic switch through the solution. The cells were then resuspended in 100 ml Dulbecco modified Eagle medium (DMEM), supplemented with 10% newborn calf serum, pencillin (100 $\mu$g/ml), streptomycin (100 $\mu$g/ml), and amphotericin B (0.25 $\mu$g/ml); and plated in four 24 well plates. Selective media was 48–78 hours after the electroporation.

The plasmids pgag-polgpt and penv were coelectroporated into 3T3 cells; as a control, 3PO and pSV2gpt were also coelectroporated into 3T3 cells. Cells were selected for the presence of the gpt gene with media containing 15 $\mu$g/ml of hypoxanthine, 250 $\mu$g/ml of xanthine and 25 $\mu$g/ml of mycophenolic acid (MA) (HXM media). Clones selected with HXM media were analyzed for reverse transcriptase (RT) production as described previously (14). Positive controls for RT activity were $\psi$2 cell (6) supernatants and supernatants from wild type Mo-MULV clone 4 cells. Negative controls for RT activity were untransfected 3T3 supernatants and RT cocktail alone.

Figure 3:
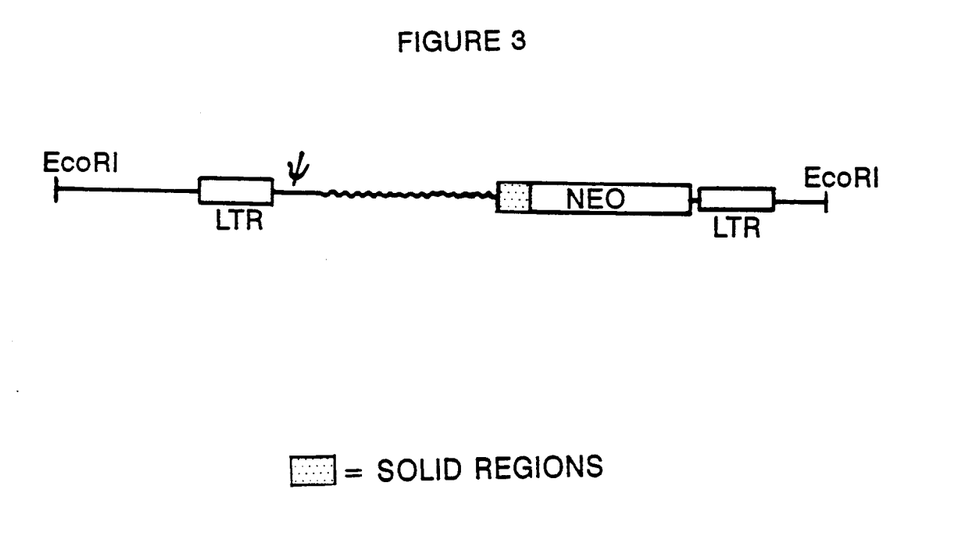
FIG. 3. Replication-defective retroviral vectors N2 and Δneo.

Packaging lines were transfected with the retroviral vector plasmids $\Delta$neo and N2 by electroporation of $10^7$ NIH 3T3 cells with 5 $\mu$g plasmid DNA. Both plasmids contain a neomycin resistance ($neo^R$) gene; eukaryotic cells expressing the gene were selected with the antibiotic G418 (800 $\mu$g/ml). $\Delta$neo is a 6.6 kb replication-defective retroviral plasmid in which the $neo^R$ gene is flanked by intact LTRs and has 5' gag sequences including an intact $\psi$ sequence (FIG. 3). (N. Lerner, personal communication) N2 has been described previously (16).

Analysis of Viral Proteins

The presence and expression of penv was analyzed by metabolic labelling and immunoprecipitation of gPr80env, the env protein, with env antiserum as follows: Clones of confluent cells (on 10 cm plates) were starved for 20 minutes in DMEM minus methionine, and 150 $\mu$c $^{35}$S methionine (Amersham) was added for 40 minutes. The cells were lysed in 1% Triton X100, 0.5% deoxycholate, 0.1% SDS, 10 mM sodium phosphate, pH 7.5, 0.1M NaCl; the cell lysate was spun down in a TI50 or TI80 rotor at 35K. for three hours at 4° C. Supernatant was incubated with normal goat serum, and nonspecifically bound proteins precipitated with pansorbin (staph A protein, Cal-Biochem). The remaining supernatant was incubated with env antiserum (NCI #795-771) overnight and the immunoprecipitates collected with pansorbin. The labelled proteins were analyzed by electrophoresis on a 10% SDS polyacrylamide gel (19) followed by fluorography.

Virus Production

Titers of colony-forming units were determined by infection of NIH 3T3 cells dilutions of viral harvest as follows: NIH 3T3 cells ($5 \times 10^5$) were seeded in a 6 cm petri dish. Eighteen hours later viral harvest supernatants from clones of semi-confluent cells were filtered through 0.45 micron filters (Millipore) and 1 ml was applied to the cells. Eight $\mu$g/ml of polybrene (Dextran) was added to the supernatants to enhance the titer. After 2 hours of 37° C., 4 ml of media was added to the cells; 48 hours later the cells were trypsinized and plated on a 10 cm plate in media containing 800 $\mu$g/ml G418; 10–14 days later clones were counted.

Generation of the Packaging Line

Figure 4:
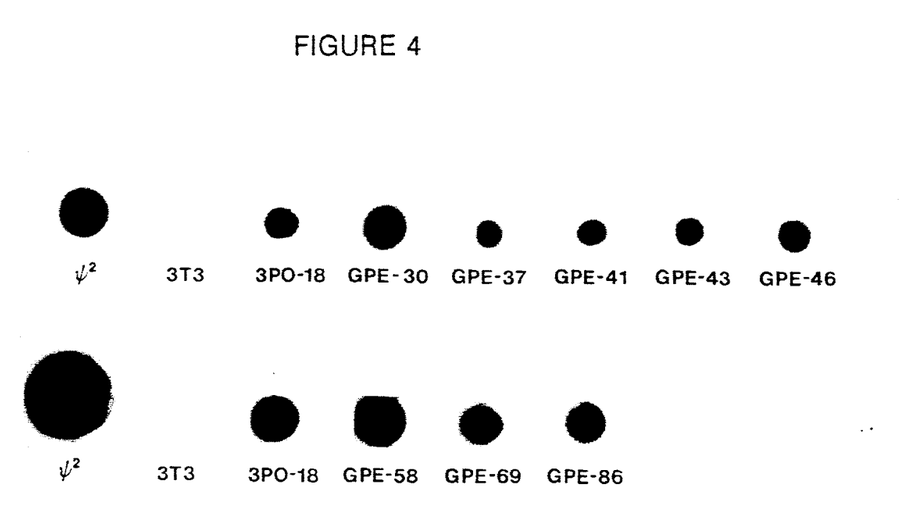
FIG. 4. RT assays of supernatants from clones of cells with 3PO or cotransfected with pgag-polgpt and penv.

To generate cell lines expressing gag-pol and env regions from different plasmids, 3T3 cells were cotransfected, by electroporation (13), with pgag-polgpt and penv DNAS. Recipient cells were then selected with media containing MA. Eighty-six MA-resistant (GP+E) clones were isolated and their supernatants tested for their ability to produce reverse transcriptase (RT), the pol gene protein. Twenty-seven clones were found to produce a high level of the reverse transcriptase produced by 3T3 cell containing the parent plasmid 3PO (FIG. 4). In a separate electroporation, 3PO DNA, containing an intact set of gag, pol, and env genes, was coelectroporated with pSV2gpt into 3T3 cells. Of 16 MA-resistant clones obtained from this electroporation and tested, supernatants from 3 were high in reverse transcriptase (FIG. 4). The reverse transcriptase levels of the high reverse transcriptase-producing GP+E clones were qqual to those of the high reverse transcriptase-producing 3PO clones.

Figure 5:
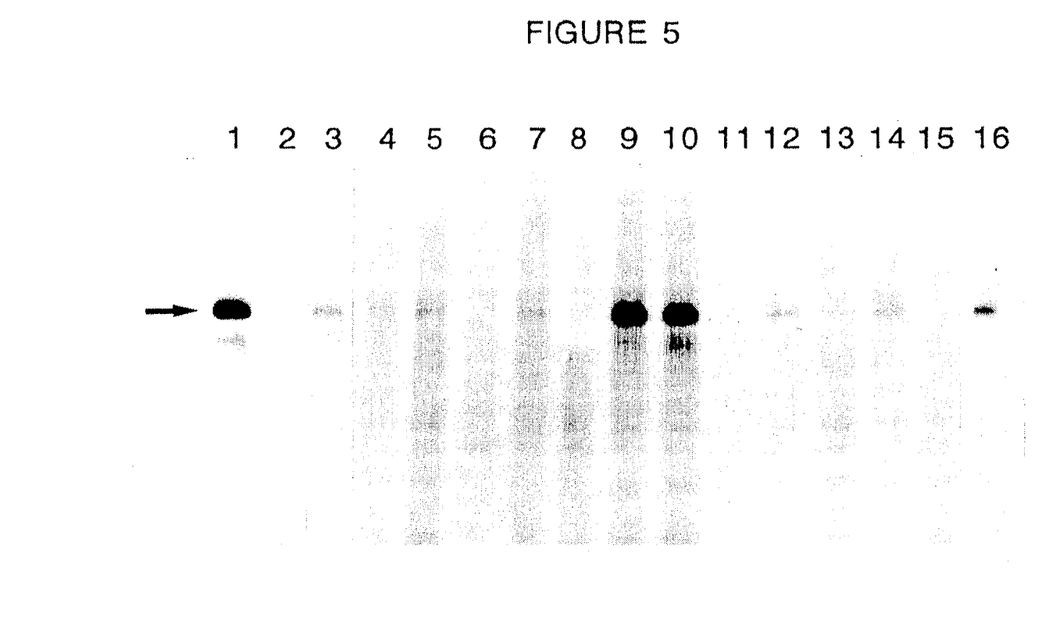
FIG. 5. Analysis of viral env protein synthesis in transfected NIH 3T3 cells.

Twenty-one of the high RT-producing GP+E clones were then analyzed for env protein expression by metabolic labelling followed by immunoprecipitation with env antiserum (15). Eleven of the clones were positive for gPr80env; 3 clones produced a strong signal, 4 a medium signal, and 4 a weak signal (FIG. 5).

Ability of Cell Lines to Package Retroviral Vectors

Five of the GP+E cell lines which expressed high reverse transcriptase activity and medium-to-high env protein were tested for their ability to package the replication-defective retroviral vector $\Delta$neo. $\Delta$neo is a 6.6 kb replication-defective retroviral plasmid containing a neomycin resistance gene driven by an SV40 promoter (FIG. 3). Cell lines were transfected with $\Delta$neo and G418-resistant clones were collected. Supernatants from G418-resistant were then tested for $\Delta$neo viral particles. The titers of GP+E$\Delta$neo clones ranged from $2 \times 10^2$ to $1.7 \times 10^5$ CFU/ml (Table 1). These titers were comparable to $\Delta$neo titers released from the 3PO-18 packaging line, which was constructed by transfecting 3PO into NIH 3T3 cells ($8 \times 10^2$ to $6.5 \times 10^4$ CFU/ml) as well as from the $\psi^2$ packaging line (6) ($4.6 \times 10^4 - 5.4 \times 10^4$ CFU/ml). The GP+E-86 packaging line produced titers that were consistently higher than the other four GP+E lines, and was therefore used in subsequent experiments.

To test the effect of changing the structure of the retroviral vector containing the exogenous gene, in this case, the neomycin-resistance gene, GP+E-86 cells were transfected with the N2 retroviral vector (16) in which neomycin-resistance expression is controlled by the viral LTR (FIG. 3). G418-resistant clones were tested for N2 virus titer, and titers of $5.0 \times 10^3$ to $4 \times 10^6$ CFU/ml were obtained (Table 1). These titers were comparable to N2 titers released from the 3PO-18 cell line ($1.85 \times 10^4$ to $5.0 \times 10^5$ CFU/ml). Thus, N2 produced titers that were 1-2 logs higher than $\Delta$neo, and the packaging line we contructed was as efficient as one in which all three retroviral components are on the same plasmid.

TABLE 1

VIRUS PRODUCTION FROM PACKAGING CELLS CONTAINING RETROVIRAL VECTORS

| Packaging Cell Line | Vector | # Clones Tested | Titer (CFU/ml) Range | Median | Mean |
|---|---|---|---|---|---|
| GP + E-86 | $\Delta$neo | 9 | $2 \times 10^2 - 1.7 \times 10^5$ | $3.3 \times 10^4$ | $5.4 \times 10^4$ |
| $\psi^2$ | $\Delta$neo | 2 | $4.6 \times 10^4 - 5.4 \times 10^4$ | NA | NA |
| 3PO-18 | $\Delta$neo | 8 | $8 \times 10^2 - 6.5 \times 10^4$ | $6.2 \times 10^3$ | $1.47 \times 10^4$ |
| GP + E-18 | N2 | 22 | $5 \times 10^3 - 4 \times 10^6$ | $7.5 \times 10^5$ | $1.38 \times 10^6$ |
| 3PO-18 | N2 | 9 | $1.85 \times 10^4 - 5 \times 10^5$ | $1 \times 10^5$ | $2.14 \times 10^5$ |
| GP + envAm-12 | N2 | 22 | $3 \times 10^3 - 1 \times 10^6$ | $6.75 \times 10^4$ | $1.45 \times 10^5$ |
| PA317 | N2 | 6 | $2 \times 10^3 - 2 \times 10^5$ | $1.15 \times 10^5$ | $1.01 \times 10^5$ |

Analysis for Recombinant Infectious Retrovirus

As a preliminary test for infectious retrovirus, supernatants from 5 high-titer GP+E+$\Delta$neo clones were used to infect 3T3 cells. The infected 3T3 cells were selected with G418 and allowed to develop into a confluent layer of G418-resistant clones. Supernatants from these plates (2° GP+E$\Delta$neo supernatants) were then used to infect fresh 3T3 cells. These 3T3 cells were again selected with G418 that resulted in no surviving G418-resistant cells. These same supernatants also tested negative for reverse transcriptase. These results indicate that there was no viral rescue of $\Delta$neo from the initial 3T3 cells infected with GP+E+$\Delta$neo primary supernatants.

As a stringent test for infectious retrovirus which may have been generated through recombination events between the two helper plasmids and the $\Delta$neo retroviral vector, 3T3 cells were infected with supernatant from pooled clones containing GP+E-86+$\Delta$neo. The infected cells were passaged continously for one month without G418 selection. This treatment would have allowed a rare wild-type virus to spread throughout the population of 3T3 cells (this population of cells should contain cells successfully infected with $\Delta$neo virus as well as uninfected 3T3 cells that are not G418-resistant), and therefore led to the spread of infectious $\Delta$neo particles. After one month in culture, supernatant was assayed for $\Delta$neo virus production by infecting fresh 3T3 cells and testing for G418 resistance. The infected 3T3 cells yielded no G418-resistant clones, indicating that there was no viral rescue of $\Delta$neo from the initial 3T3 cells that were infected with GP+E-86+$\Delta$neo supernatant.

In a different test of the safety of the GP+E-86 packaging line, supernatant from cells containing GP+E-86 was used to infect pools of N2-transfected 3T3 cells (3T3-N2 pools). If the 3T3-N2 cells became infected with wild-type virus secreted from GP+E-86 cells, the 3T3-N2 cells would begin to secrete N2 virus. Supernatant from the GP+E-86-infected 3T3-N2 pools was harvested and used to infect fresh 3T3 cells. These 3T3 cells were then tested for the presence of N2 virus by G418 selection. Using the assay we were unable to detect G418-resistant cells, demonstrating that GP+E-86 cells are unable to transfer the packaging function or to rescue N2 virus from 3T3 cells.

Construction of an Amphotropic Packaging Line

To generate a safe amphotropic packaging line we constructed the plasmid penvAm using DNA from pL1 (5), a plasmid containing the 4070A amphotropic murine Leukemia virus proviral DNA. A fragment containing the env gene and 3' acceptor splice site was isolated and ligated to a fragment from 3PO containing the Mo-MULV 5' LTR and 5' donor splice site (FIG. 1). The plasmids penvAm and pRSVhyg (17) were co-transfected into a clone of 3T3 cells that had been transfected with the pgag-polgpt and shown to produce a high level of reverse transcriptase. Hygromycin B-resistant clones were isolated and tested for amphotropic env protein production by metabolic labelling followed by immunoprecipitation with env antiserum. The cell line GP+envAm-12 was selected as a clone producing high levels of both reverse transcriptase and amphotropic env protein. To test packaging ability, GP+envAm-12 cells were transfected with N2. G418-resistant clones were isolated and the titers of released N2 virus were determined by infecting 3T3 cells with harvested supernatants. Titers of GP+envAm-12+N2 clones ranged from $3 \times 10^3$ to $>1 \times 10^6$ CFU/ml (Table 1). In a control experiment, N2 was transfected into the amphotropic packaging line PA317 (11). Titers of G418-resistant clones, when used to infect 3T3 cells, range from $2 \times 10^3$ to $2.0 \times 10^5$ CFU/ml. The results indicate that GP+envAm-12 is as efficient in retroviral gene transfer as PA317.

Use of Packaging Lines to Generate Producer Lines

Packaging cell lines can be used to construct cell lines that produce helper-free viruses which contain any gene of interest (producer lines) by transfecting retroviral vectors into them. The GP+E-86 ecotropic packaging line and the GP+envAm-12 Amphotropic packaging line can be used to generate safe producer lines as follows: The packaging cell lines are transfected with DNA containing a $\psi$ packaging sequence, a selectable marker, and the gene of interest; for example the $\beta$ globin or ADA gene. The $\psi$ packaging sequence allows the retroviral vector to be encapsidated into a virus shell using proteins synthesized in the packaging cell line. The selectable marker, such as the neomycin resistance gene, allows for selection of cells successfully transfected or infected with the vector. Individual clones, or pools of clones, containing the transfected vector are selected. These clones secrete the packaged vector virus, and not the defective helper virus, and are known as producer lines. Titering assays are then done to determine the viral titers released by the producer lines.

EXPERIMENTAL DISCUSSION

One of the requirements for the use of retroviral vectors in human gene therapy is the use of a packaging line which is incapable of producing wild-type virus. While recently-designed packaging lines are relatively safe, wild-type virus may be produced through two recombinational events between the helper virus and a replication-defective retroviral vector even with the most frequently used amphotropic line PA317. In order to create a safer packaging line, we have separated the gag and pol genes on one plasmid, and the ecotropic or amphotropic env gene on another plasmid. These plasmids contain deletions of the packaging ($\psi$) signal and the 3' LTR. We have developed an ecotropic packaging line (GP+E-86) and an amphotropic packaging line (GP+envAm-12) that produce titers of retroviral particles comparable to those packaging lines containing the helper virus genome on a single plasmid.

Both the ecotropic (GP+E-86) and the amphotropic (GP+envAm-12) packaging lines produce high gag-pol and env protein levels, as demonstrated by the reverse transcriptase assay and immunoprecipitation with $\alpha$ env. GP+E-86 cells (which contain gag and pol on one plasmid and env on another plasmid) upon transfection with the retroviral vectors Δneo and N2 release titers that are comparable to the titers released by 3PO-18 and $\psi$2 cells (which contain an intact gag-pol-env plasmid). These titers obtained are comparable to those reported by others using defective retrovirus (5, 20, 6, 11, 7, 8, 9) and are high enough for use in gene transfer experiments in animals (21, 22, 23, 24, 10, 25, 11, 26, 27).

We have found no evidence for the generation of wild-type retrovirus using the GP+E-86 packaging line, either alone or in combination with the replication-defective retroviral vectors Δneo and N2. Thus, we have found no evidence for recombinational events occuring when gag-pol on one plasmid and env on another are used in plasmids that also contain $\psi$ mutations and deletions of 3' LTRs. Cells electroporated with these packaging plasmids and then with vector plasmids do not appear to produce the three recombinational events needed for the generation of wild type virus. Preliminary experiments also demonstrate that the GP+envAm-12 packaging line appears to be equally safe and therefore appropriate for use in experiments designed for human gene therapy.

REFERENCES

1. Cone, R. D., A. Weber-Benarous, D. Baorto, and R. C. Mulligan. 1987. Regulated expression of a complete human B-globin gene encoded by a transmissible retrovirus vector. *Mol. Cell. Biol.* 7:887–897.
2. Anderson, W. F. 1984. Prospects for human gene therapy. *Science* 226:401–409.
3. Neel, B. B., W. S. Hayward, H. L. Robinson, J. Fang, and S. M. Astrin. 1981. Avian leukosis virus-induced tumors have common proviral integration sites and synthesize discrete new RNAS: Oncogenesis by promoter insertion. *Cell* 23:323–334.
4. Varmus, H. E., N. Quintrell, and S. Ortiz. 1981. Retroviruses as mutagens: Insertion and excision of a nontransforming provirus alter expression of a resident transforming provirus. *Cell* 25:23–36.
5. Cone, R. D., and R. C. Mulligan. 1984. High efficiency gene transfer into mammalian cells: Generation of helper-free retrovirus with broad mammalian host range. *Proc. Natl. Acad. Sci.* 81:6349–6353.
6. Mann, R., F. C. Mulligan, and D. Baltimore. 1983. Construction of a retrovirus packaging mutant and its use to produce helper-free defective retrovirus. *Cell* 33:153–159.
7. Miller, A. D, M. -F. Law, and I. M. Verma. 1985. Generation of helper-free Amphotropic retroviruses that transduce a dominant-acting methotrexate-resistant dihydrofolate reductase gene. *Mol. Cell Biol.* 5:431–437.
8. Sorge, J., D. Wright, V. D. Erdman, and A. Cutting. 1984. Amphotropic retrovirus system for human cell gene transfer. *Mol. Cell. Biol.* 4:1730–1737.

9. Watanabe, S., and H. M. Temin. 1983. Construction of a helper cell line for Avian reticuloendotheliosis virus cloning vectors. *Mol. Cell. Biol.* 3:2241-2249.

10. Hock, R. A., and A. D. Miller. 1986. Retrovirus-mediated transfer and expression of drug-resistant genes in human haematopoietic progenitor cells. *Nature* 320:257-277.

11. Miller, A. D., and C. Buttimore. 1986. Redesign of retrovirus packaging cell lines to avoid recombination leading to helper virus production. *Mol. Cell. Biol.* 6:2895-2902.

12. Mulligan, R. C., and P. Berg. 1980. Expression of a bacterial gene in mammalian cells. *Science* 209:175-183.

13. Potter, H., L. W. Weir, and P. Leder. 1984. Enhancer-dependent expression of human K immunoglobulin genes introduced into mouse pre-B lymphocytes by electroporation. *Proc. Natl. Acad. Sci.* 81:7161-7165.

14. Goff, S. P., P. Traktman, and D. Baltimore. 1981. Isolation and properties of Moloney murine leukemia virus mutants: Use of a rapid assay for release of virion reverse transcriptase. *J. Virol.* 38:239-248.

15. Schwartzberg, P., J. Colicelli, and S. Goff. 1983. Deletion mutants of Maloney murine leukemia virus which lack glycosylated gag protein are replication competent. *J. Virol.* 46:538-546.

16. Keller, G., C. Paige, E. Gilboa, and E. F. Wagner. 1985. Expression of a foreign gene in myeloid and lymphoid cells derived from multipotent haematopoietic precursors. *Nature* 318:149-154.

17. Murphy, A. J. 1987. Molecular techniques for the isolation of transcriptional transacting genes. Doctoral Thesis, Columbia University 133-139.

18. Grunstein, M., and D. S. Hogness. 1975. Colony hybridization: A method for isolation of cloned DNAs that contain a specific gene. *Proc. Natl. Acad. Sci.* 72:3961-3965.

19. Laemmli, U. K. 1970. Cleavage of structural proteins during the assembly of the head of bacteriophage T4. *Nature* 227:680-685.

20. Cone, R. D., A. Weber-Benarous, D. Baorto and R. C. Mulligan. 1987. Regulated expression of a complete human β globin gene encoded by a transmissible retrovirus vector. *Mol. Cell. Biol.* 7:887-897.

21. Cline, M. J., H. Stang, K. Mercola, L. Morse, R. Ruprecht, J. Browne, and W. Salser. 1980. Gene transfer in intact animals. *Nature* 284:422-425.

22. Dick, J. E., M. C. Magli, D. Huszar, R. A. Phillips and A. Bernstein. 1985. Introduction of a selectable gene into primitive stem cells of long-term reconstitution of the hemopoietic system of W/W$^V$ mice. *Cell* 42:71-79.

23. Eglitis, M. A., P. Kantoff, E. Gilboa, and W. F. Anderson. 1985. Gene expression in mice after high efficiency retroviral-mediated gene transfer. *Science* 230:1395-1398.

24. Gruber, H. E., K. D. Finley, R. M. Herschberg, S. S. Katzman, P. K. Laikind, J. E. Seegmiller, T. Friedman, J. Yee and D. J. Jolly. 1985. Retroviral vector-mediated gene transfer into human hematopoietic progenitor cells. *Science* 230:1057-1060.

25. Lemischka, I. R., D. H. Raulet, and R. C. Mulligan. 1986. Developmental potential and dynamic behavior of hematopoietic stem cells. *Cell* 45:917-927.

26. Williams, D. A., I. R. Lemischka, D. G. Nathan and R. C. Mulligan. 1984. Introduction of new genetic material into pluripotent haematopoietic stem cells of the mouse. *Nature* 310:476-480.

27. Williams, D. A., S. H. Orkin and R. C. Mulligan. 1986. Retrovirus-mediated transfer of human adenosine deaminase gene sequences into cells in culture and into murine hematopoietic cells in vivo. *Proc. Natl. Acad. Sci.* 83:2566-2570.

What is claimed is:

1. The ecotropic cell line designated GP+E-86 (ATCC Accession No. CRL 9642).

2. The amphotropic cell line designated GP+envAm-12 (ATCC Accession No. CRL 9641).

3. A process for generating a producer cell line useful for transferring a gene of interest into recipient mammalian cells comprising transfecting cells of the cell line of claim 31 or 32 with a vector plasmid which comprises a psi packaging sequence, a gene associated with a selectable or identifiable phenotypic trait which is manifested when the plasmid is present in a transfected cell, and a gene of interest.

4. The process of claim 3, wherein the vector plasmid is Δneo.

5. The process of claim 3 wherein the vector plasmid is N2.

6. The process of claim 3, wherein the phenotypic trait is drug resistance.

7. The process of claim 6, wherein the drug resistance is neomycin resistance.

8. The producer cell produced by the process of claim 3.

9. A method for transferring a gene of interest into recipient mammalian cells comprising:
 (a) transfecting cells of the cell line of claim 31 or 32 with a vector plasmid which comprises a psi packaging sequence, a gene associated with a selectable or identifiable phenotypic trait which is manifested when the plasmid is present in a transfected cell, and a gene of interest, so as to generate producer cells;
 (b) isolating producer cells from mammalian cells which secrete the selectable marker contained within the vector;
 (c) separating the isolated producer cells from the secreted vector; and
 (d) contacting the secreted vector with a recipient mammalian cell thereby transferring a gene of interest into recipient mammalian cells.

* * * * *